United States Patent [19]

Mazur

[11] 3,975,365

[45] Aug. 17, 1976

[54] INHIBITORY OCTAPEPTIDES ANGIOTENSIN II

[75] Inventor: Robert H. Mazur, Deerfield, Ill.

[73] Assignee: G. D. Searle & Co., Chicago, Ill.

[22] Filed: Jan. 27, 1975

[21] Appl. No.: 544,128

[52] U.S. Cl. .......................... 260/112.5 R; 424/177
[51] Int. Cl.$^2$ ................ C07C 103/52; A61K 37/00
[58] Field of Search ............................ 260/112.5 R

[56] References Cited
UNITED STATES PATENTS 3,886,134   5/1975   Sipos et al.................... 260/112.5 R

OTHER PUBLICATIONS

Khairallah et al., J. Med. Chem., 13, 181–184 (1970).

Primary Examiner—Lewis Gotts
Assistant Examiner—Reginald J. Suyat
Attorney, Agent, or Firm—John J. McDonnell

[57]   ABSTRACT

Octapeptide derivatives characterized by an oxygen or sulfur-containing moiety in the C-terminal position are potent inhibitors of the pharmacological effects of Angiotensin and possess the additional advantage of a favorable antagonist/agonist ratio.

14 Claims, No Drawings

INHIBITORY OCTAPEPTIDES ANGIOTENSIN II

The present invention is concerned with novel octapeptide derivatives characterized by an oxygen or sulfur-containing moiety in the C-terminal position and, more particularly, with compounds of the following structural formula

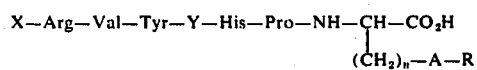

Wherein X represents a sarcosine or aspartic acid residue, Y is the residue of isoleucine or valine, $n$ is a positive integer less than 4, A is O, S, SO, or $SO_2$, and R is lower alkyl having 1–7 carbon atoms, or arylakyl of the formula

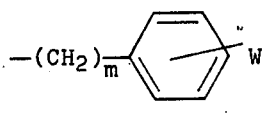

wherein $m$ is 1 or 2 and W is hydrogen, halo, loweralkyl having 1–7 carbon atoms, or loweralkoxy having 1–7 carbon atoms.

Embodiments of the formula

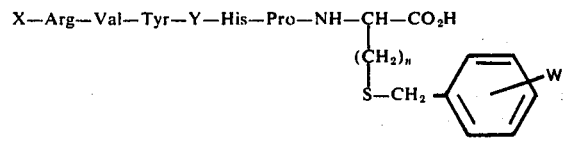

wherein X represents an aspartic acid or sarcosine residue, Y represents an isoleucine or valine residue, W represents hydrogen or halo, $n$ is 1 or 2, and the amino acid residues have L or DL stereochemical configuration are preferred. These embodiments are exemplified by

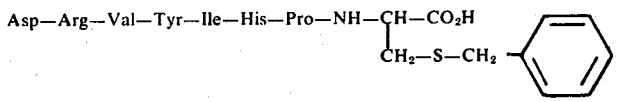

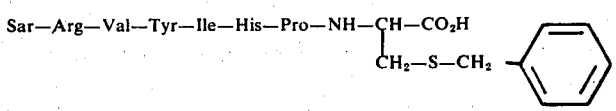

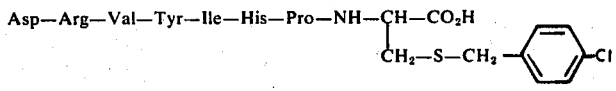

with L-aspartyl-L-arginyl-L-valyl-L-tyrosyl-L-isoleucyl-L-histidyl-L-prolyl-S-benzyl-L-cysteine, L-sarcosyl-L-arginyl-L-valyl-L-tyrosyl-L-isoleucyl-L-histidyl-L-prolyl-S-benzyl-L-cysteine, L-aspartyl-L-arginyl-L-valyl-L-tyrosyl-L-isoleucyl-L-histidyl-L-prolyl-S-(p-chlorobenzyl)-L-cysteine being the most preferred compounds.

Embodiments in which X, Y, and A are as earlier defined and R is alkyl having 1–7 carbon atoms exemplified by R= —$CH_3$ and —$C(CH_3)_3$ with the preferred R = alkyl embodiments being compounds of the formula

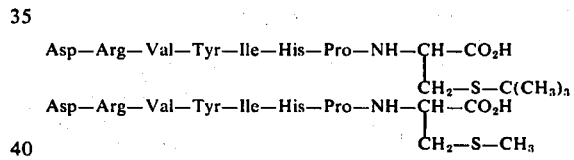

Embodiments in which X, Y, and R are as earlier defined in the broadest sense and A is $SO_2$ or SO are exemplified by

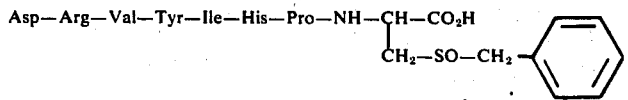

and

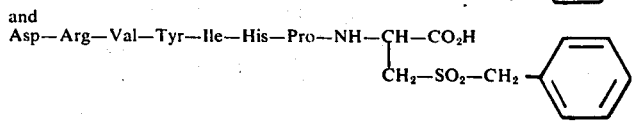

with the latter being preferred.

A preferred embodiment in which A = O is

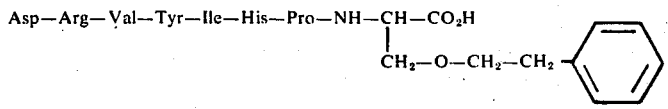

Abbreviations connote the amino acids defined in accordance with the nomenclature rules published by the IUPAC-IUB Commission on Biochemical Nomenclature at *Archives of Biochemistry and Biophysics*, 150, 1–8 (1972). The amino acids may have the L or DL sterochemical configuration.

The halo radicals encompassed by the R substituent are typified by chloro, bromo, fluoro and iodo.

The compounds of the present invention are pharmacological agents particularly useful as Angiotensin inhibitors and are additionally advantageous in view of their favorable antagonist/agonist ratio. Their inhibitory property is demonstrated by activity in the following assay procedures:

Virgin female Charles River rats weighing 200–250 g. are injected 24 and 48 hours before use with diethyl stilbesterol, 1 mg./kg. subcutaneously, dissolved in corn oil. The rats are sacrificed by cervical dislocation and the uterus is removed and a section of the uterine horns mounted in a 2 ml. tissue bath containing a modified Tyrode solution maintained at 30°C. and bubbled with 95% oxygen, 5% carbon dioxide. A series of control contractions is elicited by alternate additions of angiotensin II, antidiuretic hormone (ADH) and bradykinin. A solution of the test compound is then substituted for the plain Tyrode solution and the "treat" contractions are obtained after an equilibration period of 15 or 30 minutes. Regularly timed contractions are elicited during the equilibration period in order to maintain the timed sequence of agonist additions. Three control and three treat contractions are averaged to obtain the mean percent change. The compound is rated active if it effects a significant decrease in the contractions produced by the action of the agonist.

Blood pressure is measured in Charles River albino rats anesthetized with pentobarbital sodium (50 mg./kg.) and pretreated with phenoxybenzamine (30 mg./kg.) and propanolol (15 mg./kg.) while maintaining body temperature at 32°C. The pressure is recorded from the carotid artery with a P-100 linear core pressure transducer, Physiograph. Both jugular veins are cannulated; one vein used for infusion of antagonists and the other for bolus injections of angiotensin II. An angiotensin II dose response curve is determined before each test of the antagonists so that each animal serves as its own control. An additional group of animals is tested to determine the effects of a 15 minute placebo infusion of saline on angiotensin II responses. After determination of the angiotensin II dose response curve, a placebo or inhibitor infusion is initiated and maintained at 15 minutes. Immediately after the infusion period the dose response curve is repeated. In the case of angiotensin II the dose response curve is determined during the infusion and then immediately after in an attempt to determine the duration of the inhibition. Relative activity is determined by comparing the ratio of the calculated doses of angiotensin II necessary to increase blood pressure 25 mm. of mercury before and after the inhibitor.

A group of 7 rabbits is prepared surgically with chronic indwelling aortic and venus catheters by a modification of the method of Bazaral et al., *J. Appl. Physiol.*, 29, 113, (1970). The rabbits are allowed to recover from surgery, during which time they are periodically brought into the laboratory in order to accustom them to handling and to the necessary restraining procedures. Blood pressure is measured by the aortic catheter and injections are made by the jugular catheter. Blood pressure responses are recorded on a 4 channel Brush Recorder (Model 440).

On the day of the test the animals are attached to the recording equipment and allowed to stabilize for at least 30–60 minutes before commencement of the injections. Control responses are obtained with Angiotensin II administered intravenously at a dose of 1 mcg./kg. before intramuscular administration of the test compound.

The doses of agonist are repeated at 10, 20, 30, 40, 50, 60, 75, 90, 120, 150 and 180 minutes following each dose of the test compound. The mean responses at each time period are calculated for each treatment and are compared statistically with the control mean using Student's $t$ test at the 95% level of confidence ($P < 0.05$). The compound is rated active if it inhibits the activity of the agonist at the aforementioned statistical level of confidence.

The manufacture of the instant novel compounds is conveniently achieved by processes usually adapted to the synthesis of peptides. Thus, the C-terminal amino acid, optionally substituted with protecting groups, is coupled with an active ester of the appropriate N-protected amino acid to afford the corresponding N-protected dipeptide. Removal of the N-protecting group is followed, similarly, by coupling with the active ester of the N-protected amino acid required to produce the desired tripeptide. This sequential procedure is repeated until the desired octapeptide derivative is produced. As a specific example, S-benzyl-L-cysteine is coupled with tertiary-butoxycarbonyl-L-proline 2,4,5-trichlorophenyl ester in the presence of N-methylmorpholine; the resulting N-(tertiary-butoxycarbonyl)-L-prolyl-S-benzyl-L-cysteine is treated with trifluoroacetic acid to afford the trifluoroacetic acid salt of L-prolyl-S-benzyl-L-cysteine; the latter material is coupled, in the manner as previously described with α,im-di-(tertiary-butoxycarbonyl)-L-histidine 2,4,5-trichlorophenyl ester to yield the protected tripeptide and this procedure is successively repeated to afford, after removal of the protecting groups, L-aspartyl-L-arginyl-L-valyl-L-tyrosyl-L-isoleucyl-L-histidyl-L-prolyl-S-benzyl-L-cysteine.

The aforementioned procedures are preferably carried out in accordance with standard organic chemical techniques, whereby each intermediate peptide is produced as described hereinbefore and isolated prior to coupling with the next appropriate N-protected amino acid active ester. Alternatively, this sequential process can be conducted by solid phase peptide synthesis, which consists of first attaching to a polymer support, e.g. chloro=methylated copylystyrene-1% divinylbenzene polymer, the optionally N-protected C-terminal amino acid, followed by removal of the N-protecting group and coupling, in the presence of a suitable reagent, e.g. dicyclohexylcarbodi=imide, successively with each of the appropriate N-protected amino acids.

The invention will appear more fully from the examples which follow. These examples are given by way of illustration only and are not to be construed as limiting the invention either in spirit or in scope, as many modifications both in materials and in methods will be apparent to those skilled in the art. In these examples temperatures are given in degrees Centigrade, (°C.) and quantities of materials in parts by weight unless otherwise noted.

EXAMPLE 1

S-Benzylcysteine (211 parts) is suspended in 2000 parts by volume of dimethyl formamide and 101 parts of N-methylmorpholine added. t-Butoxycarbonylproline 2,4,5-trichlorophenyl ester (434 parts) is added and the mixture stirred 48 hours at room temperature.

A clear solution results. Most of the dimethylformamide distilled off under high vacuum at 40°. The residual sirup is diluted with 2000 parts by volume of ethyl acetate. The solution washed four times with 2000 parts by volume, portions of 0.2M potassium bisulfate, the organic layer is dried over sodium sulfate, and the ethyl acetate distilled off under reduced pressure. The residue is shaken with ether to give a white powder, 368 parts (90%). The product is identified by its nuclear magnetic resonance spectrum to have the structure

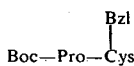

40.8 Parts of this material is dissolved in 200 parts by volume of ice cold trifluoroacetic acid. The initially vigorous gas evolution subsides after about 15 minutes and the solution is allowed to stand one hour at room temperature. The trifluoroacetic (TFA) is distilled off under vacuum and the residue rubbed with ether. Pro-(Bzl)Cys·TFA is obtained as a white solid.

The above salt, Pro-(Bzl)Cys·TFA 42.2 parts, is dissolved in 220 parts by volume of dimethylformamide and 20.2 parts of N-methylmorpholine is added. To the clear solution is then added 58.8 parts of α, im-di-t-butoxycar=bonylhistidine-2,4,5-trichlorophenyl ester and the reaction is allowed to proceed 24 hours at room temperature. Thin layer chromatography shows that all the prolyl-S-benzylcys=teine is reacted. The dimethylformamide is distilled off under high vacuum at 40° and the residual gum is dissolved in 1000 parts by volume of ethyl acetate. The ethyl acetate is washed four times with 1 l. portions of 0.2 M potassium bisulfate, dried over sodium sulfate and stripped under vacuum. The residue is dissolved in 100 parts by volume of ethyl acetate and is dripped into 2000 parts by volume of ether with very rapid stirring. The resulting white powder is

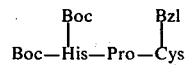

This product, α, im-di-t-butoxy-carbonyl-histydyl=λ prolyl-S-benzylcysteine (64.5 parts), is dissolved in 65 parts by volume of dioxane, cooled to 0° and 130 parts by volume of 6M hydrogen chloride in dioxane is added with vigorous stirring. After a few minutes, the product begins to crystallize. After stirring for two hours at room temperature, the product is filtered and washed with 500 parts by volume of dioxane to provide

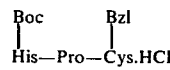

Carbobenzoxytyrosine 2,4,5-trichlorophenyl ester (544 parts) is added to a suspension of 131 parts of isoleucine in 2000 parts by volume of dimethylformamide. After adding 101 parts of N-methylmorpholine, the mixture is stirred 48 hours at room temperature. Unreacted isoleucine is still present. Water (500 parts by volume) is added and stirring is continued for another 48 hours. The mixture is concentrated to dryness under high vacuum at 40°. The residue is dissolved in 2000 parts by volume of ethyl acetate, the ethyl acetate is washed with four 2000 parts by volume portions of 0.2 M potassium bisulfate, dried over sodium sulfate and stripped under reduced pressure. The residue is dissolved in 1 l. of chloroform and the solution added dropwise with violent stirring to 20 l. of ether. The resulting white powder, carbobenzoxy=tyrosylisoleucine, (42.8 parts) 0.1 mole, is dissolved in 500 parts by volume of 90% acetic acid and hydrogenated at 60 psi at room temperature over 4.3 parts of palladium black. Hydrogen uptake stopped after 2 hours. The catalyst is filtered off and the filtrate concentrated to dryness under vacuum. The residue is rubbed with ether yielding tyrosylisoleucine, Tyr-Ile.

Tyrosylisoleucine (29.4 parts) is suspended in 300 parts by volume of dimethyl sulfoxide and 10.1 parts of N-methylmorpholine added. Carbobenzoxyvaline-2,4,5-trichlorophenyl ester is added and the mixture stirred 48 hours at room temperature. The clear solution is poured into 6000 parts by volume of 0.1 N hydrochloric acid and the mixture is stirred until the initially oily product solidifies. The crude product, after washing with water and drying, is boiled with 1 l. of ether. The desired tri-peptide, Z-Val-Tyr-Ile, is obtained as a white powder.

This protected tripeptide (52.7 parts) is dissolved in 500 parts by volume of 90% acetic acid and hydrogenated over 5.3 parts of palladium black at room temperature and 60 psi. After removing the catalyst, the solution is stripped to dryness and the residue rubbed with 1 l. of ether. The desired product, valyl=λ tyrosylisoleucine, Val-Tyr-Ile, is obtained.

α-Carbobenzoxy-G,G-diisobornyloxycarbonylar=ginine-2,4,5-trichlorophenyl ester (93.2 parts) is dissolved in 1 l. of dimethylformamide. Valyltyrosyl=isoleucine (39.3 parts) are added followed by 10.1 parts of N-methylmorpholine. The mixture is stirred 48 hours at room temperature. The resulting clear solution is concentrated to a gum at 40° under high vacuum. The residue is dissolved in 2000 parts by volume of ethyl acetate, the ethyl acetate is washed four times with 0.2 M potassium bisulfate, and dried over sodium sulfate. The ethyl acetate is stripped off under reduced pressure and the residue shaken with ether to give a white powder having the structure

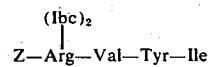

Protected tetrapeptide (104.3 parts) is dissolved in 2000 parts by volume of 90% acetic acid and hydrogenated over 10.5 parts of palladium black at 60 psi and room temperature. After hydrogen uptake ceases, the catalyst is removed and the solvents removed under vacuum. The residue was rubbed with ether to yield G,G-diisobornyloxycarbonylarginylvalyltyrosylisoleucine, having the following structure

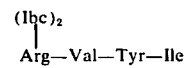

The above tetrapeptide (90.0 parts), carboben=zoxyaspartic acid α-2,4,5-trichlorophenyl ester β-t-butyl ester (55.3 parts) and 10.1 parts of N-methylmorpholine are dissolved in 1000 parts by volume of dimethylformamide. The solution is allowed to stand 24 hours at room temperature. The dimethylformamide is removed under high vacuum at 40° and the residue dissolved in 2000 parts by volume of ethyl acetate. The ethyl acetate is washed four times with 0.2 M potassium bisulfate, dried over sodium sulfate and stripped under vacuum. The residue is stirred and heated with 2000 parts by volume of ether to provide carbobenzoxy-β-t-butylaspartyl-G,G-diisobornyloxycarbonyl-arginyl-valyltyrosylisoleucine, having the following structure

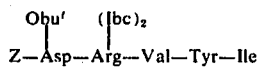

12.14 Parts of this protected peptide is dissolved in 120 ml. of DMF and 1.73 parts of N-hydroxysuccinimide is added. The solution is cooled to 0° and 2.27 parts of dicyclohexylcarbodiimide added. The solution is stirred 4 hours at room temperature. After a few minutes dicyclohexylurea begins to precipitate.

To the crude active ester having the structure

OBu' (Ibc)₂
|     |
Z—Asp—Arg—Val—Tyr—Ile—OSu is added 5.82 parts of im-t-butoxycarbonylhistidylprolyl-S-benzylcysteine hydrochloride followed by 2.02 parts of N-methylmorpholine. The mixture is stirred 48 hours at room temperature. Thin layer chromatography shows that there is no change during the last 24 hours and that a small amount of the C-terminal tripeptide remains. The mixture is filtered to remove dicyclohexylurea and the filtrate concentrated to dryness under high vacuum at 40°. The residue is dissolved in 100 parts by volume of methanol and the solution added to 2000 parts by volume of 0.2 M potassium bisulfate with rapid stirring. The resulting powder is filtered, washed with 2000 parts by volume of water and dried to provide the crude angiotensin analog,

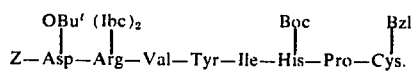

The crude peptide (2.00 parts) is purified by countercurrent distribution in n-butanolacetic acid — water 4:1:5 using an automatic apparatus with 240 tubes and three ml. phases. To separate the desired product from impurities requires 960 transfers. The recovery of homogeneous material, after pooling and stripping appropriate fractions, is 1.41 parts. On this basis, the final coupling step gives a yield of 68%. The NMR spectrum of this product is consistent with the desired structure.

The above protected octapeptide (1.219 parts) is dissolved in 24 parts of acetic acid and 12 parts by volume of 6 M hydrogen bromide in acetic acid is added. The solution is stirred one hour at room temperature and concentrated to dryness under reduced pressure. The residue is solidified under ether. The resulting hydrobromide is dissolved in a minimum volume of water and applied to a column containing 100 parts of IRC-50, a carboxylicacid cation exchange resin. The octapeptide is obtained by linear gradient elution using zero to one hundred percent acetic acid. The total volume of solvent is three l. and ten ml. fractions are collected.

The fractions containing pure material are pooled and the solvents removed under vacuum. The residue is dissolved in 50 parts of water and the solution lyophilized to provide a compound of the formula

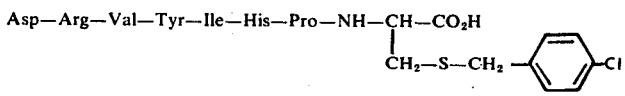

Using the respective L- amino acids provides L-aspartyl-L-arginyl-L-valyl-L-tyrosyl-L-isolencyl-L-histidyl-L-prolyl-S-benzyl-L-cysteine as a white fluffy powder.

EXAMPLE 2

Incorporating S-(p-chlorobenzyl)cysteine in the procedure set out in Example 1 provides a compound of the formula Asp—Arg—Val—Tyr—Ile—His—Pro—NH—CH—CO₂H
                                      |
                                      CH₂—S—CH₂—⟨C₆H₄⟩—Cl Using the respective L- amino acids provides L-aspartyl-L-arginyl-L-valyl-L-tyrosyl-L-isoleucyl-L-histidyl-L-prolyl-S-(p-chlorobenzyl)-L-cysteine.

EXAMPLE 3

Incorporation of sarcosine for aspartic acid and valine for isoleucine in the synthetic scheme set out in Example 1 provides a compound of the formula

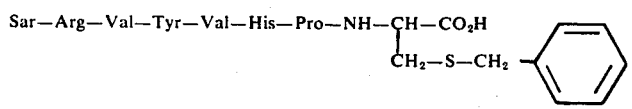

Using the respective L- amino acids provides sarcosyl-L-arginyl-L-valyl-L-tyrosyl-L-valyl-L-histidyl-L-prolyl-S-benzyl-L-cysteine.

EXAMPLE 4

Incorporating S-(p-methoxybenzyl)cysteine in the procedure set out in Example 1 provides a compound of the formula

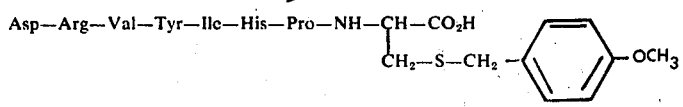

Using the respective L- amino acids provides L-aspartyl-L-arginyl-L-valyl-L-tyrosyl-L-isoleucyl-L-histidyl-L-prolyl-L-(p-methoxybenzyl)-L-cysteine.

EXAMPLE 5

Incorporating S-(p-ethoxybenzyl)cysteine in the procedure set out in Example 1 provides a compound of the formula

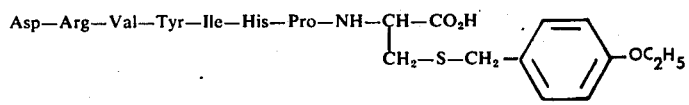

Using the respective L- amino acids provides L-aspartyl-L-arginyl-L-valyl-L-tyrosol-L-isoleucyl-L-histidyl-L-prolyl-S-(p-ethoxybenzyl)-L-cysteine.

EXAMPLE 6

Incorporating S-(p-methylbenzyl)cysteine in the procedure set out in Example 1 provides a compound of the formula

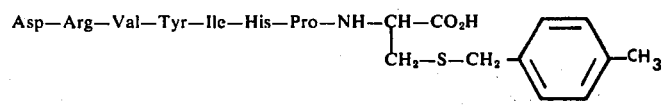

Using the respective L-amino acids provides L-aspartyl-L-arginyl-L-valyl-L-tyrosyl-L-isoleucyl-L-histidyl-L-prolyl-S-(p-methylbenzyl)-L-cysteine.

EXAMPLE 7

Incorporating S-(p-ethylbenzyl)cysteine in the procedure set out in Example 1 provides a compound of the formula

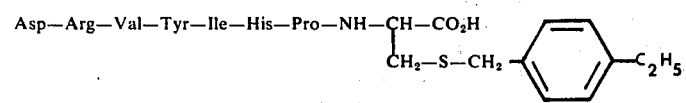

Using the respective L- amino acids provides L-aspartyl-L-arginyl-L-valyl-L-tyrosyl-L-isoleucyl-L-histidyl-L-prolyl-S-(p-ethylbenzyl)-L-cysteine.

EXAMPLE 8

Incorporating S-(p-bromobenzyl)cysteine in the procedure set out in Example 1 provides a compound of the formula

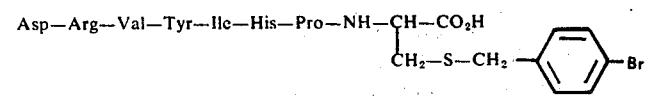

Using the respective L- amino acids provides L-aspartyl-L-arginyl-L-valyl-L-tyrosyl-L-isoleucyl-L-histidyl-L-prolyl-S-(p-bromobenzyl)-L-cysteine.

EXAMPLE 9

L-O-(2-phenethyl)-serine is prepared as follows:
Methyl acrylate, (86 parts) is dissolved in 1800 parts of carbon tetrachloride and 160 parts of bromine are added dropwise to the solution with cooling and stirring over a period of 2 hours. After stirring for an additional hour, the solvent is removed under high vacuum at room temperature to provide methyl-2,3-dibromopropionate.

Sodium metal (23.0 parts) is dissolved in 147 parts of 2-phenylethanol by warming and stirring. Anhydrous dimethylformamide (2000 parts by volume) is added to give a suspension of the sodium salt of 2-phenylethanol. The crude methyl 2,3-dibromopropionate is added and the suspension is stirred for 2 days at 100°. The solvent is removed under high vacuum at 40°.

The oily residue is shaken with 2000 parts by volume of ethyl acetate and 2000 parts by volume of 1 molar potassium bisulfate and this organic layer is washed 4 times with water. The organic layer is dried over sodium sulfate and the ethylacetate is removed under vacuum. The residual liquid is used in the next step:

Total crude ester from the previous reaction is dissolved in 2000 parts by volume of acetone, the solution cooled in an ice bath and 2000 parts by volume of 1 molar sodium hydroxide added dropwise with stirring. The clear solution is allowed to stand 2 hours at room temperature and the acetone removed under vacuum.

The solution containing the sodium salt of 2-bromo-3-(2-phenylethoxy)-propionic acid is washed with ether, strongly acidified with concentrated hydrochloric acid, and the product taken up in ethylacetate. The ethylacetate is washed 5 times with water, dried over sodium sulfate, and removed under vacuum.

Total crude bromo acid is dissolved in 2000 parts by volume of concentrated ammonium hydroxide and the solution heated 24 hours at 100° in an autoclave. The cooled solution is taken to dryness under vacuum. The residue is crystallized from 1000 parts by volume of 50% ethanol. This procedure removes ammonium bromide and provides DL-O-(2-phenethyl)-serine.

Phenethylserine (105 parts) is dissolved in 500 parts by volume of 1 normal sodium hydroxide. Acetic anhydride (102 parts) is added dropwise with cooling and stirring while maintaining pH11 with 4 normal sodium hydroxide. The solution is stirred 1 hour after completion of the addition and acidified to pH2 with concentrated hydrochloric acid. The product is crystallized and is filtered and washed thoroughly with water to provide N-acetyl-DL-O-(2-phenethyl)-serine.

Taka diastase (250 parts) is stirred very rapidly with 500 parts by volume of water for 1 hour at room temperature. The mixture is filtered through Supercel and the filter cake rinsed with water. N-acetyl-DL-O-(2-phenethyl)-serine (125 parts) is suspended in 250 parts by volume of water and brought into solution with 2 normal lithium hydroxide. The combined enzyme filtrates are added, the pH adjusted to 7.0, and the solution incubated at 40° for one week. The solution was acidified to pH 5.5, concentrated under vacuum to about 250 parts by volume and diluted with 250 parts by volume of ethyl alcohol. The product was filtered and washed with 50% ethyl alchhol to give optically pure L-phenethylserine. D-acetylphenethylserine can be recovered from the filtrate.

Incorporating O-(2-phenethyl)-serine in the procedure set out in Example 1 provides a compound of the formula

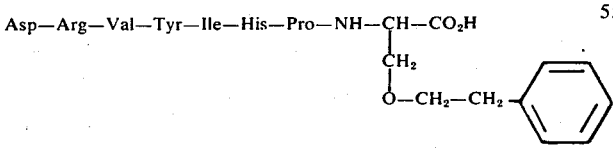

Using the respective L-amino acids provides L-aspartyl-L-arginyl-L-valyl-L-tyrosyl-L-isoleucyl-L-histidyl-L-prolyl-L-O-(2-phenethyl)-serine.

What is claimed is:
1. A compound of the formula

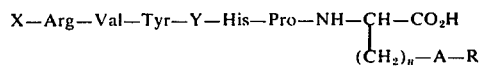

wherein X represents a sarcosine or aspartic acid residue, Y represents the residue of isoleucine or valine, $n$ is 1, A is O, S, SO, $SO_2$, and R is arylalkyl of the formula

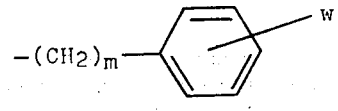

wherein $m$ is 1 or 2, $w$ is hydrogen, halo, loweralkyl having 1–7 carbon atoms, or loweralkoxy having 1–7 carbon atoms, and the amino acid residues having L or DL stereochemical configuration.

2. As in claim 1, a compound of the formula

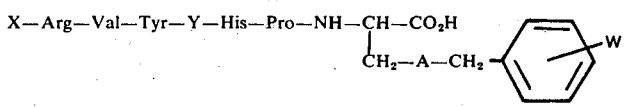

wherein X represents a sarcosine or aspartic acid residue, Y represents the residue of isoleucine or valine, A represents O, S, SO, or $SO_2$, $w$ is hydrogen, halo, loweralkyl having 1–7 carbon atoms or loweralkoxy having 1–7 carbon atoms and the amino acid residues having the L or DL stereochemical configuration.

3. As in claim 1, a compound of the formula

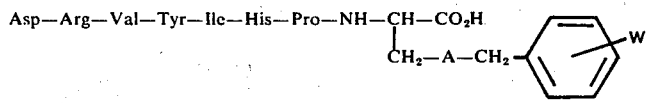

wherein A represents O, S, SO, or $SO_2$ and $w$ represents hydrogen, halo, loweralkyl having 1–7 carbon atoms or loweralkoxy having 1–7 carbon atoms.

4. The compound according to claim 1 wherein A represents S, $w$ represents hydrogen or halo.

5. The compound according to claim 1 wherein R is loweralkyl having 1–7 carbon atoms and the amino acids having L or DL stereochemical configuration.

6. A compound according to claim 1, wherein the amino acids have the L stereochemical configuration.

7. A compound according to claim 1, wherein X represents an aspartic acid residue.

8. A compound according to claim 1, wherein X represents a sarcosine residue.

9. A compound according to claim 1, wherein Y represents an isoleucine residue.

10. A compound according to claim 1, wherein Y represents a valine residue.

11. The compound according to claim 1 which is L-aspartyl-L-arginyl-L-valyl-L-tyrosyl-L-isoleucyl-L-histidyl-L-prolyl-S-benzyl-L-cysteine.

12. The compound according to claim 1 which is sarcosyl-L-arginyl-L-valyl-L-tyrosyl-L-isoleucyl-L-histidyl-L-prolyl-S-benzyl-L-cysteine.

13. The compound according to claim 1 which is L-aspartyl-L-arginyl-L-valyl-L-tyrosyl-L-isoleucyl-L-histidyl-L-prolyl-S-(p-chlorobenzyl)-L-cysteine.

14. The compound according to claim 1 which is L-aspartyl-L-arginyl-L-valyl-L-tyrosyl-L-isoleucyl-L-histidyl-L-prolyl-L-O-(2-phenethyl)-serine.

* * * * *